United States Patent [19]
Bennett et al.

[11] Patent Number: 5,213,098
[45] Date of Patent: May 25, 1993

[54] POST-EXTRASYSTOLIC POTENTIATION STIMULATION WITH PHYSIOLOGIC SENSOR FEEDBACK

[75] Inventors: Tom D. Bennett, Shoreview; Russell L. Lundstrom, Jr., Minneapolis; Paul M. Stein, Maple Grove, all of Minn.

[73] Assignee: Medtronic, Inc., Minneapolis, Minn.

[21] Appl. No.: 736,198

[22] Filed: Jul. 26, 1991

[51] Int. Cl.⁵ .......................................... A61N 1/365
[52] U.S. Cl. ................................................ 128/419 PG
[58] Field of Search ................................ 128/419 PG

[56] References Cited

U.S. PATENT DOCUMENTS

| | | |
|---|---|---|
| 3,683,934 | 8/1972 | Bukowiecki et al. ......... 128/419 PG |
| 3,857,399 | 12/1974 | Zacouto ..................... 128/419 P |
| 3,920,024 | 11/1975 | Bowers ...................... 128/419 PG |
| 3,939,844 | 2/1976 | Pequig330523 ................. 128/419 P |
| 4,055,189 | 10/1977 | Auerbach et al. ........... 128/419 PG |
| 4,088,140 | 5/1978 | Rockland et al. ............. 128/419 PG |
| 4,181,133 | 1/1980 | Kolenik et al. ............... 128/419 PG |
| 4,253,466 | 3/1981 | Hartlaub et al. ............. 128/419 PG |
| 4,280,502 | 7/1981 | Baker, Jr. et al. ............. 128/419 PG |
| 4,373,531 | 2/1983 | Wittkampf et al. ........... 128/419 PG |
| 4,407,296 | 10/1983 | Anderson ............................. 128/675 |
| 4,452,248 | 6/1984 | Keller, Jr. .................... 128/419 PG |
| 4,467,807 | 8/1984 | Bornzin ........................ 128/419 PG |
| 4,485,813 | 12/1984 | Anderson et al. ............... 128/419 P |
| 4,522,208 | 6/1985 | Buffet .......................... 128/419 PG |
| 4,541,433 | 9/1985 | Baudino ............................. 128/668 |
| 4,570,495 | 2/1986 | Terada ............................. 73/864.25 |
| 4,596,251 | 6/1986 | Plicchi et al. ................. 128/419 PG |
| 4,730,389 | 3/1988 | Baudino et al. .............. 128/419 PG |
| 4,730,619 | 3/1988 | Koning et al. ................ 128/419 PG |
| 4,770,177 | 9/1988 | Schroeppel ................... 128/419 PG |
| 4,791,931 | 12/1988 | Slate ........................... 128/419 PG |
| 4,807,629 | 2/1989 | Baudino et al. .............. 128/419 PG |
| 4,813,421 | 3/1989 | Baudino et al. ..................... 128/633 |
| 4,899,751 | 2/1990 | Cohen .......................... 128/419 PG |
| 4,903,701 | 2/1990 | Moore et al. ................. 128/419 PG |
| 4,945,909 | 8/1990 | Fearnot et al. .............. 128/419 PG |
| 4,986,270 | 1/1991 | Cohen .......................... 128/419 PG |

OTHER PUBLICATIONS

*Cardiac Pacemakers* by Harold Siddons and Edgar Sowton, M.D., 1968 pp. 201–216.
"Manual Model 5837 R-Wave Coupled Pulse Generator", Medtronic, Inc. Preliminary Edition III, Jul. 1965 (TC 65 076) 17 pp.
"The Hemodynamic Effect of Slowing the Heart Rate by Paired or Coupled Stimulation of Article", In *American Heart Journal*, vol. 73, No. 3, pp. 362–368, Mar. 1967 by John W. Liser.
"Electro-Augmentation of Ventricular Performance and Oxygen Consumption by Repetitive Application of Paired Electrical Stimuli in Circulation Research", by John Ross, Jr., M.D., et al. vol. 16, pp. 332–342, Apr. 1965.

*Primary Examiner*—William E. Kamm
*Attorney, Agent, or Firm*—Dwight N. Holmbo; Harold R. Patton

[57] ABSTRACT

A post-extrasystolic potentiation (PESP) cardiac pacing energy stimulator for applying paired and/or triggered pacing stimulation pulses to the right atrium and/or ventricle incorporating one or more sensors, such as a venous oxygen saturation, ventricular, atrial, or arterial blood pressure, or intracardiac or systemic blood flow sensor, and signal processing circuitry for controlling the frequency of or number of heart cycles between periodic delivery of triggered or paired pacing to induce PESP for the treatment of congestive heart failure or other cardiac dysfunctions. Preferably, a first sensor, e.g., a ventricular or arterial blood pressure or flow sensor, is employed to monitor the performance of the heart, and develop a cardiac performance index (CPI) and a second sensor, e.g., an oxygen saturation sensor positioned in the coronary sinus, is employed to monitor cardiac muscle stress and develop a cardiac stress index (CSI) to balance performance and stress. The PESP stimulator may be incorporated into a dual chamber (DDD) pacing system with or without physiologic rate control and with or without backup cardioversion/defibrillation therapy capabilities or in a separate, single purpose device. The PESP stimulator has particular application in atrial stimulation for augmenting filling of the ventricles.

28 Claims, 8 Drawing Sheets

POST-EXTRASYSTOLIC POTENTIATION STIMULATION WITH PHYSIOLOGIC SENSOR FEEDBACK

BACKGROUND OF THE INVENTION

1. Field of the Invention

This invention relates to the application of paired and/or coupled pacing stimulation to effect post-extrasystolic potentiation (PESP) cardiac output augmentation with physiologic sensor feedback for reducing cardiac muscle fatigue and the risk of inducing life threatening arrhythmias.

2. Description of a Prior Art

Atrioventricular (AV) synchronous pacing systems, including DDD pacing systems marketed by Medtronic, Inc. and other companies, have been prescribed for treatment of a variety of bradycardia conditions in patients, including, in certain instances, patients suffering from congestive heart failure. Such patient groups tend to do much better hemodynamically with AV synchronous pacing due to the added contribution of atrial contraction to ventricular filling and subsequent contraction. However, fixed or physiologic sensor driven rate responsive pacing in such patients does not always lead to improvement in cardiac output and alleviation of the symptoms attendant to such disease processes. Several forms of heart failure are also associated with compromised diastolic function and/or decreased atrial and ventricular compliance. These may be conditions associated with chronic disease processes or complications from cardiac surgery with or without specific disease processes. Most heart failure patients do not normally suffer from a defect in the conduction system leading to ventricular bradycardia, but rather suffer from symptoms which may include a general weakening of the contractility of the cardiac muscle, attendant enlargement thereof, depressed ventricular filling characteristics, edema, and disruption in systemic blood pressure. All these disease processes lead to insufficient cardiac output to sustain even moderate levels of exercise and proper function of other body organs. Such patients are normally treated with drug therapies, including digitalis, which may lead to toxicity and loss of effectiveness.

In the early days of implantable cardiac pacing, it was observed that paired and triggered (also referred to as coupled) pacing with relative short interpulse intervals (150 to 250 milliseconds in dogs and about 300 milliseconds in human subjects) results in electrical depolarizations without attendant mechanical myocardial contractions. The result of the second pulse, applied within the relative refractory period of the first paced or spontaneous depolarization, is to prolong the refractory period and effect a slowing of the heart rate from its spontaneous rhythm. This slowing effect has been employed since that time in many applications, including the treatment of atrial and ventricular tachycardias, where a single pulse or a burst of pulses are coupled to a spontaneous tachycardia event with a coupling interval that is shorter than and can be set as a fraction of the tachycardia interval as taught, for example, in U.S. Pat. No. 3,857,399 to Dr. Fred Zacouto and U.S. Pat. No. 3,939,844 to Michael Pequiguot. The slowing of the heart rate by coupled pacing is accompanied by the ability to increase or decrease the rate with subsequent paired pacing within wide limits.

Paired and coupled stimulation also cause a potentiation of contractile force effect through a phenomenon known as post-extrasystolic potentiation. The effect can be performed continuously provided there is a continuous string of extrasystoles. When removed, the effect decays over the next few contractions until the base line levels of force production are reached. The extent of the potentiation is closely related to the prematurity of the extrasystole.

Early investigators conducted a large number of animal and human studies employing paired and coupled stimulation of the atrial and ventricular chambers in an effort to employ the PESP effect for the ventricles therapeutically. A history of the investigations and studies conducted in the 1960's is published in the book *Cardiac Pacemakers* by Harold Siddons and Edgar Sowton, M.D., 1968, pages 201–216 and the bibliography listing articles referenced therein. In addition, medical device manufacturers, including Medtronic, Inc., offered paired and coupled pacing pulse stimulators over many years to investigators conducting such studies. The Medtronic® Model 5837 R-wave coupled pulse generator is an example of such non-implanted pulse generators which were used by investigators to conduct paired and coupled pacing studies where both the pacing rate and the coupling intervals were manually adjustable.

In the studies conducted with such systems, and as reported in the above-referenced Siddons et al. book and papers referenced therein, it was also observed that PESP effect is more marked in animals and patients when myocardial function is poor rather than normal. It was also observed that the "electro-augmentation" of the force of contraction provided by the PESP effect is not increased by a third electrical stimulus. Thus, usually only a second pacing pulse, either paired with a preceding pacing pulse or as triggered by a preceding spontaneous cardiac event, was employed in further studies. Such studies have included the delivery of paired or triggered pacing pulses to either the ventricle or the atrium. It was observed that in those patients that have normal AV conduction, the ventricular rate could be slowed by paired or coupled stimulation of the atrium. However, the ventricular contraction was not found to be electro-augmented by such atrial stimulation.

Other physiologic effects of the paired and coupled pacing included in the PESP effects described above attendant changes in the contractile force of the myocardium are the peak systolic blood pressure, the rate of contraction of the ventricular muscle with a resulting increase of the rate of rise of intraventricular pressure (dP/dt), an increase in coronary blood flow, and an increase in the oxygen uptake of the heart per beat. Investigators observed that PESP was accompanied by an increase in the myocardial oxygen consumption of 35% to 70% as compared with single pulse stimulation at the same rate. The addition of a third stimulus increased the myocardial oxygen uptake even further without any attendant observed increase in cardiac contractile force. The alterations in coronary flow roughly parallel the oxygen consumption of the heart as observed in such studies.

The marked potentiation effect produced by paired stimulation led certain investigators to study the use of the technique in the treatment of acute heart failure induced in dogs. Improvements in left ventricular performance and cardiac output produced by such paired pacing in these dogs was observed by several investigators. In other studies conducted on relatively normal dogs' hearts, it was confirmed that paired pacing offered no increase in cardiac output, most likely due to reflex compensation.

The above described observations from the Siddons book also appear in part in the articles "The Hemodynamic Effect of Slowing the Heart Rate by Paired or Coupled Stimulation of the Atria," *American Heart Journal*, Vol. 73, No. 3, pp. 362–368, March, 1967, by John W. Lister, M.D., et al., and "Electro-augmentation of Ventricular Performance and Oxygen Consumption by Repetitive Application of Paired Electrical Stimuli," *Circulation Research*, Vol. 16, pp. 332–342, April, 1965, by John Ross, Jr., M.D., et al.

Investigations on human subjects in those years had been less promising, at least with respect to the potentiation treatment of patients in severe congestive heart failure. In certain reported cases, however, some improvement was observed. Many of these preliminary studies in humans were conducted usually in patients whose disease state and medication (or lack thereof) rendered their hearts overly susceptible to ventricular fibrillation. It was concluded at that time that, because the second pulse of each pair had to be applied at or close to the vulnerable period in the cardiac cycle (outside the absolute refractory period, but inside the relative refractory period), the risk of provocation of ventricular fibrillation was unacceptably high in a patient whose fibrillation threshold was low. Moreover, it was observed that the fibrillation threshold varied considerably under the influence of hypoxia, electrolyte disorders, drugs, and other factors.

In addition, sophisticated implantable pulse generators and sensors were unavailable at the time and the implantation usually entailed open chest surgery to affix epicardial electrodes, which was contra-indicated in severely ill congestive heart failure patients.

The period of takeover of the ventricular rhythm by the paired or coupled stimulation was believed to be especially risky inasmuch as the vulnerable period in the cardiac cycle varied with the prematurity of an extrasystolic beat or the underlying cardiac rate. Since the length of the refractory interval was initially unknown, investigators working with a patient had to detect the end of the absolute refractory interval by trial and error, and oft times delivered the paired or coupled pulse into the vulnerable period. In addition, most physicians found these procedures and long-term patient care to be excessively time-consuming.

It should be noted that with the pacing technology at that time, the pacing threshold was close to the fibrillation threshold. In any case, the difficulty and perceived degree of risk with fairly primitive technology discouraged physicians from further considering paired and coupled pacing to augment ventricular cardiac function in congestive heart failure patients.

The most striking improvements were observed in reducing the heart rate in patients suffering from runs of either atrial or ventricular tachycardia which could not be controlled by drugs. Subsequent developments in manually initiated or automatic triggering of fixed rate or rate adaptive overdrive burst and scanning pacing have been incorporated in antitachycardia control devices including multi-programmable, multi-function cardiac pacemakers and pacemaker-cardioverter-defibrillator devices. However, little further work appears to have been conducted in regard to the use of paired and coupled stimulation to induce the PESP effects in the treatment of patients suffering from cardiac disease processes not amenable to treatment by conventional pacing or higher energy stimulation. In addition, the use of atrial paired or coupled pacing in the attempt to "potentiate" atrial cardiac contractions to produce atrial PESP effects remain incomplete.

SUMMARY OF THE INVENTION

It is thus an object of the present invention to provide an automatic cardiac stimulator capable of enhancing and/or optimizing cardiac performance in patients having poor cardiac function.

It is a further object of the present invention to provide PESP and its electro-augmentation effects as an acute therapy for patients with acutely compromised cardiac function from disease, surgery, or other traumatic insult to the myocardium, including myocardial infarction on a periodic basis, wherein the periodicity of application of stimulation is controlled as a function of one or more physiologic parameters of the cardiovascular system.

It is a still further object of the present invention to implement PESP stimulation in an atrial-ventricular pacing system wherein paired and/or triggered stimulation may be delivered only as necessary to maintain cardiac output as detected by one or more physiologic sensor.

These and other objects of the present invention are realized in a method and apparatus for providing paired and/or triggered stimulation in response to sensor detected variables related to myocardial oxygen consumption, mixed venus oxygen saturation, systemic or pulmonary blood flow, and/or ventricular, atrial, or arterial blood pressure reflecting cardiac stress and/or performance. Moreover, the method and apparatus of the present invention may be implemented in a system providing backup therapies for the treatment of induced tachyarrhythmias.

In one embodiment, a method of operating a cardiac pacemaker to provide post-extrasystolic potentiation effects to augment filling of the ventricular chambers of the heart comprises providing pacing stimuli on demand to the atrium of the heart and providing paired or triggered pacing stimulation timed from an immediately preceding pacing pulse or sensed atrial depolarization, respectively, sufficient to effect post-extrasystolic potentiation of the atrium while falling within the refractory period of the ventricle, whereby ventricular filling is augmented by the more vigorous contraction of the atrium.

In this and further preferred embodiments, either or both the stress placed on the cardiac muscle and the cardiac output performance affected by PESP may be selectively monitored by the aforementioned sensors to control the ratio of paired and triggered stimulation to the total number of paced and sensed events in a series of such events in order to control or balance stress and/or performance. Alternatively, the coupling interval between paired and triggered stimulation measured from the preceding event may be varied to increase or decrease PESP effects in order to control or balance stress and/or performance.

All of the preferred embodiments may be implemented in dual chamber pacemakers or arrhythmia control devices.

BRIEF DESCRIPTION OF THE DRAWINGS

The above and still further objects, features, and advantages of the present invention will become apparent in the following detailed description of the presently preferred embodiments, taken in conjunction with the accompanying drawings, and, in which.

DETAILED DESCRIPTION OF THE PREFERRED EMBODIMENTS

The present invention is described herein in relation to the preferred modes of single and dual chamber pacing systems as well as pacemaker-cardioverter-defibrillator systems implying sensors measuring oxygen saturation level in myocardial venous blood, arterial or ventricular pulse pressure, or other physiologic signals representative of the state of the cardiovascular system described in the above-cited prior art. It will be understood that the preferred embodiments of the present invention may be implemented in pre-existing hardware and/or software controlled systems referenced hereinafter in conjunction with specific feedback signal processing circuitry described hereinafter.

Patients who would be candidates for the implantation of systems based on the preferred embodiments of the present invention may exhibit a compromised oxygen delivery to the heart muscle due to vascular diseases such as atherosclerosis. Measurement of the oxygen saturation of the heart or other physiologic parameter varying with cardiac muscle stress provides a first physiologic variable that may be used to control the PESP stimulation to prevent overexertion of the heart muscle. A second measurement by a second sensor of a parameter varying with cardiac output may be employed to monitor system performance to also control the PESP stimulation.

In addition, such patients are susceptible to experiencing angina that could be a result of increased oxygen requirements induced by the PESP therapy. In accordance with the present invention, preferred embodiments incorporate a therapy termination control device that may be used by the patient to communicate with the implanted device to limit PESP stimulation.

Other indications for use and application of the invention are described in conjunction with the description of each of the preferred embodiments.

Figure 1:
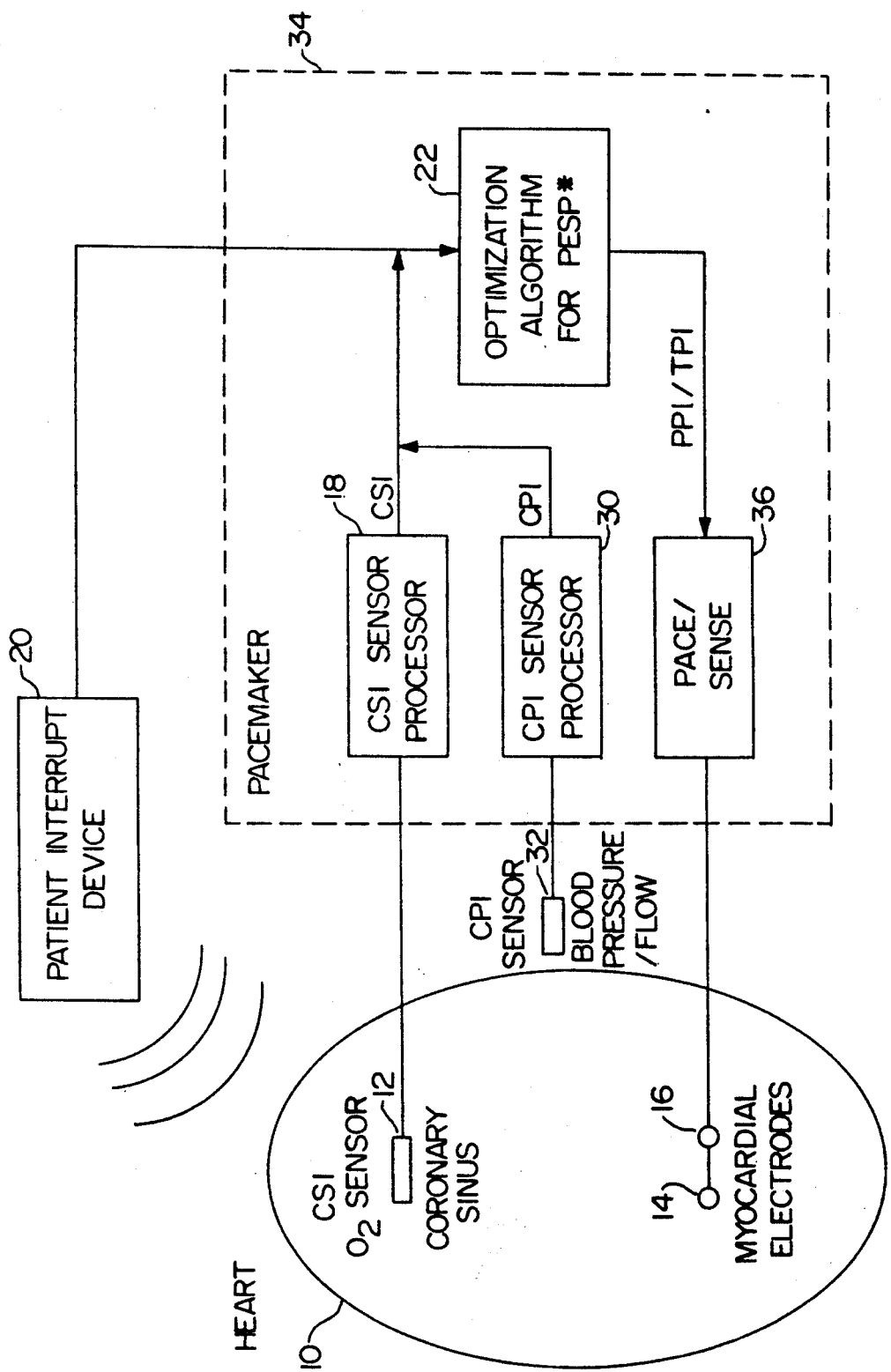
FIG. 1 is a simplified block diagram of a simple, single chamber pacing system for providing paired and coupled stimulation of the heart in proportion to a sensor output signal.

Turning now to FIG. 1, a simplified single channel system possessing such a patient interrupt and employing an oxygen saturation sensor for developing the cardiac stress index (CSI) feedback control signal to regulate the frequency of application of PESP stimulation is depicted.

FIG. 1 may be implemented in a similar fashion to and employ sensors common to the typical prior art physiologic controlled single chamber pacing system of the type shown and described in Medtronic U.S. Pat. No. 4,467,807 to Bornzin, incorporated herein by reference. In the FIG. 1 system, the pacemaker 34 includes the conventional pace/sense block 36 of the type disclosed in the '807 patent adapted to be coupled to a pair of pace/sense electrodes 14, 16. In addition, in a specific application to the method and apparatus of the present invention, a patient interrupt device 20, adapted to receive a control signal from the patient is coupled to or incorporated within the pacemaker 34. In a simplified system, the patient interrupt device may constitute a reed switch incorporated within the housing of the pacemaker 34 which may be closed or opened by magnetic field applied over the implanted device by the patient in order to interrupt the application of paired or coupled stimulation in the event that the patient feels an onset of angina. Paired and triggered stimulation induce the PESP augmentation of cardiac output, but may induce transient angina due to the enhanced oxygen utilization of the cardiac muscle which may be prevented by restrictive cardiac arteries.

The specific pacing function of the block diagram of FIG. 1 may be characterized as an AAT-R pacing system where the atrium is paced and the atrial events are sensed and stimulation is triggered in dependence upon one or both physiologic variables represented by the letter R. However, while the system may be implemented with underlying pacing rate dependent on a physiologic variable, in the context of the present invention, the physiologic signals are employed to regulate the frequency of generation of paired or triggered stimulation or the paired and triggered pacing intervals (PPI and TPI) which may be independent of the then prevailing lower rate pacing escape interval. That is to say that in a AAT pacing system, the delivery of a pacing pulse is triggered by the timeout of the A—A escape interval or sensing of a P-wave within the A—A escape interval. In the context of the present invention, the timeout of the A—A escape interval triggers the delivery of a pair of closely spaced pacing pulses having an interpulse interval (PPI) sufficient to obtain PESP effects. Similarly, the sensing of a P-wave outside the refractory and blanking intervals (a "sensed event") initiated by the preceding ventricular paired or triggered stimulation pulse triggers the delivery of a triggered stimulation pulse within the triggered pulse interval (TPI) to obtain the PESP effects of coupled stimulation. These functions may be performed by conventional single chamber pacing escape interval timers, sense amplifiers, and pulse generators, all included in block 36 coupled to electrodes 14, 16 and receiving the PESP control signal from block 22.

The CSI sensor 12 located in the coronary sinus of the patient's heart 10 is preferably an oxygen sensor coupled to oxygen saturation detection circuitry block 18 which may take the form of the sensor and signal processing circuitry depicted and described in the incorporated '807 patent as well as in the Medtronic U.S. Pat. No. 4,570,495 to Moore, et al., also incorporated herein by reference. Suffice it to say that the sensed oxygen saturation percentage may be derived in the oxygen saturation block 18 and employed as the cardiac stress index (CSI) in the optimization algorithm for PESP stimulation block 22 to regulate the frequency of PESP stimulation by block 24 in a manner to be described in conjunction with FIGS. 5-8.

Advantageously, a blood pressure or flow sensor may be included in the embodiment of FIG. 1 and in the other embodiments of the invention. In such a system, the pressure or flow sensor would be located in a suitable blood vessel or heart chamber to sense a cardiac output performance related parameter which is processed to develop a further cardiac performance index (CPI) control signal for the frequency or ratio of application of paired or coupled stimulation to paced or sensed events in one or both chambers of the heart.

The CPI signal processing block 30 is provided in the system depicted in FIG. 1 to monitor the systemic output of oxygenated blood as reflected by changes in the blood pressure, flow, or oxygen saturation in the heart or systemic veins or systemic or pulmonary arteries. The CPI sensor 32 may be a blood pressure, flow, or oxygen saturation sensor positioned within the right or left atrium or ventricle or systemic or pulmonary arteries or veins of any of the known types, including those operating on piezoelectric, piezoresistive, Doppler ultrasound, and impedance plethysmography principles, including those described in U.S. Pat. Nos. 4,770,177 to Schroeppel, 4,791,931 to Slate, 4,899,751 to Cohen, 4,730,619 to Koning et al., 4,541,433 to Baudino, 4,407,296 to Anderson, 4,485,813 to Anderson et al., 4,467,807 to Bornzin, 4,750,495 to Moore et al., 4,730,389 to Baudino et al., 4,807,629 to Baudino et al., 4,813,421 to Baudino et al., and 4,903,701 to Moore et al., all incorporated herein by reference in their entirety.

The processing of the arterial, venous, or right or left atrial or ventricular pressure signals, including the rate of change (dP/dt), mean long term and current, peak amplitude velocity or volumetric flow thereof, may be accomplished using algorithms set forth in the above-incorporated patents or in the commonly assigned, U.S. Pat. No. 5,154,170, issued Oct. 13, 1992 to Bennett et al. In any case, the processing in block 30 develops a performance optimization pacing rate control signal for setting the current escape interval that establishes the asynchronous pacing rate.

In the preferred pacing system of FIG. 1 (also implementable in FIGS. 2 and 3 as a subset of possible operating modes), the frequency or coupling interval control signal for the PESP stimulation is established by CSI sensor 12 and signal processing block 18 modified by the CPI sensor 32 and signal processing block 30.

In the context of the present invention, the CSI signal alone or together with the CPI signal is employed to inhibit the delivery of the paired or triggered pulse by block 36 in proportion to the detected stress/performance levels. Thus, it is contemplated that at certain CSI/CPI levels, not every paired or triggered pulse in a series of pacing and sensing events would be delivered. As CSI increases, a greater proportion of paired or triggered pulses would be inhibited, so that the patient may enjoy the effects of PESP stimulation increased cardiac output without inducing oxygen starvation and its attendant risks of inducing angina pain or tachyarrhythmias.

Alternatively, it has been observed that the degree of PESP, i.e., the amount of the electro-augmentation, is dependent on the paired or coupled pulse interval. That is, as the PPI or TPI (hereinafter "PPI/TPI") is foreshortened or extended beyond a peak response interval, the contractile force response diminishes. Thus, it is contemplated that the PPI/TPI itself may be varied as a function of the sensed CSI/CPI level to increase or decrease the PESP effect and attendant oxygen uptake by the cardiac muscle. In this embodiment, it would not be necessary to adjust the ratio of paired or triggered to non-paired or coupled stimulation events. It is also contemplated that both techniques could be employed with preference first given to varying the PPI and/or TPI or the proportion of paired or triggered pulses to total paced and sensed events.

Figure 2:
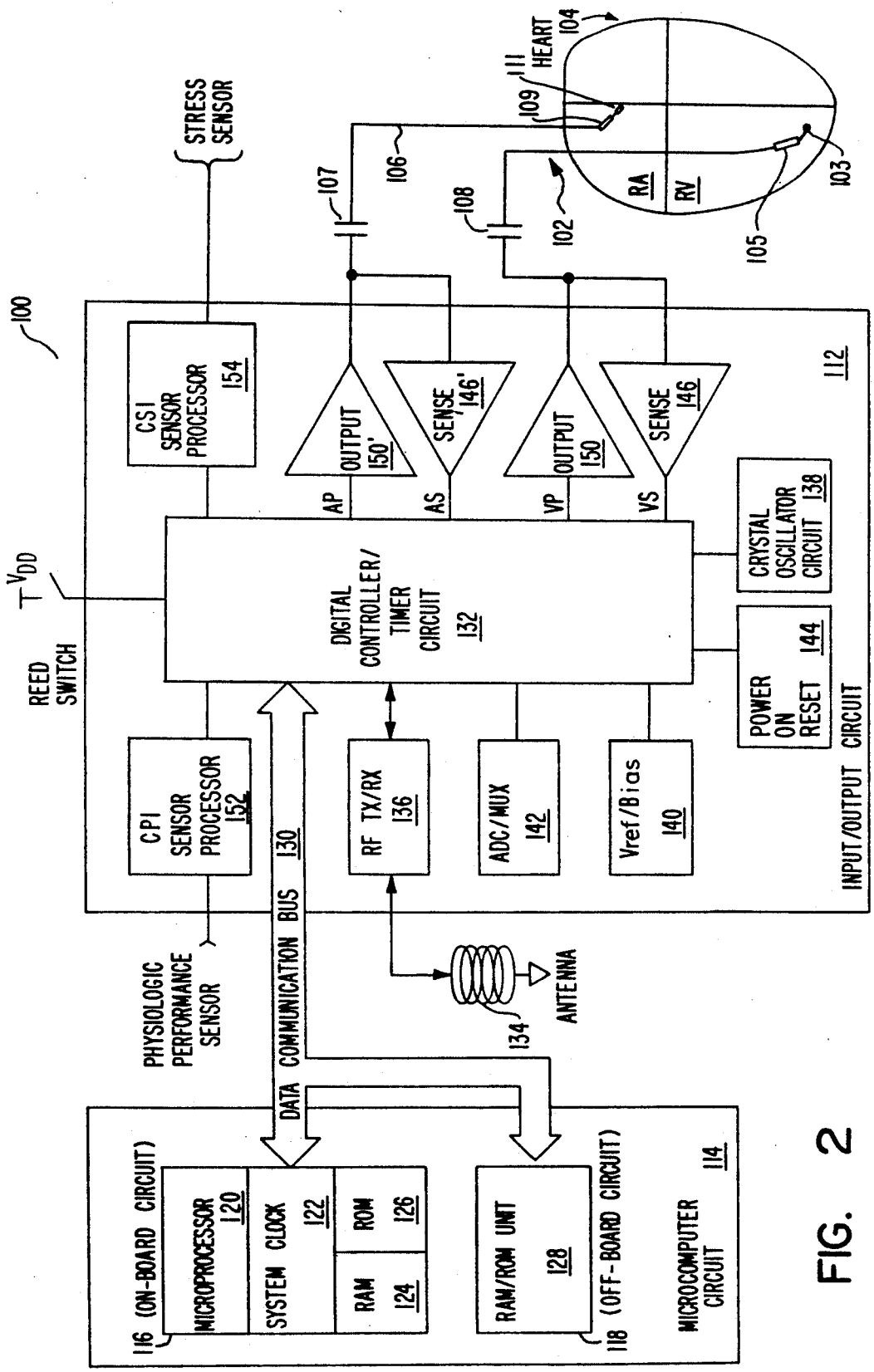
FIG. 2 is a simplified block diagram of a dual chamber pacing system in which the PESP stimulation of the present invention may be implemented.

Turning now to FIG. 2, a rate-responsive, dual chamber pacing system implementing the method and apparatus of the present invention is depicted. The system of FIG. 2 is a modification of the system disclosed in Medtronic U.S. Pat. No. 5,154,170, issued Oct. 13, 1992 to Bennett et al. and incorporated herein by reference. The system at FIG. 2 is implemented with a microcomputer circuit 114, an input/output circuit 112, data communication bus 130 and resident software for receiving and processing atrial and ventricular P-waves and R-waves, a signal derived from the aforementioned and incorporated oxygen sensor for measuring cardiac muscle stress and pressure or flow sensor(s) for measuring system performance and controlling the pacing rate and an antenna 134 and transceiver 136 for receiving programming signals from an external programmer/transceiver (not shown) and transmitting data to the programmer/transceiver on receipt of an appropriate telemetry out command.

In the embodiment of FIG. 2, the pacemaker circuit 100 is schematically shown electrically coupled via pacing leads 102 and 106 to a patient's heart 104. Lead 102 includes bipolar electrodes 103 and 105 at the distal end of lead 102 and positioned within the right ventricle (RV) of the patient's heart 104. Lead 106 also includes bipolar electrodes 109 and 111 positioned in the right atrium. Leads 102 and 106 can carry either unipolar or bipolar electrodes as is well known in the art. Electrodes 103, 105 and 109, 111 are coupled via suitable conductors in leads 102, 106 through output capacitors 108, 107 to input/output terminals of an input/output circuit 112.

The input/output circuit 112 contains the operating input and output analog circuits for digital controlling and timing circuit 132 necessary for the detection of electrical signals derived from the heart, such as the P-wave and the R-wave, as well as for the application of atrial and/or ventricular stimulating pulses to the heart to control its rate under the control of software-implemented algorithms in a microcomputer circuit 114 and control and data signals traversing data bus 130.

Microcomputer circuit 114 comprises an on-board circuit 116 and an off-board circuit 118. On-board circuit 116 includes a microprocessor 120, a system clock 122, and on-board RAM 124 and ROM 126. Off-board circuit 118 includes an off-board RAM/ROM Unit 128. Microcomputer circuit 114 is coupled by data communication bus 130 to a digital controller/timer circuit shown at 132. Microcomputer circuit 114 may be fabricated of custom IC devices augmented by standard RAM/ROM components. It will be understood that the electrical components represented in FIG. 2 are powered by an appropriate implantable-grade battery power source (not shown).

An antenna 134 is connected to input/output circuit 112 for purposes of uplink/downlink telemetry through an RF transmitter/ receiver circuit (RF TX/RX) shown at 136. Telemetering both analog and digital data between antenna 134 and an external device, such as an external programmer (not shown), is accomplished in the preferred embodiment by means of all data first being digitally encoded and then pulse position modulated on a damped RF carrier, as substantially described in U.S. Pat. No. 5,127,404 issued Jul. 7, 1992 and assigned to the assignee of the present invention.

A crystal oscillator circuit 138, typically a 32,768 Hz crystal-controlled oscillator, provides main timing clock signals to digital controller/timer circuit 132. A Vref/bias circuit 140 generates a stable voltage reference and bias currents for the analog circuits of input-/output circuit 112. An ADC/multiplexer circuit (ADC/MUX) 142 digitizes analog signals and voltages to provide telemetry and replacement time indicating function (EOL). A power-on-reset circuit (POR) 144 functions as a means to reset circuit and related functions to a default condition upon detection of a low battery condition, which will occur upon initial device power-up or transiently occur in the presence of electromagnetic interference, for example.

The operating commands for controlling the timing of the pacemaker depicted in FIG. 1 are coupled by bus 130 to digital controller/timer circuit 132 wherein digital timers set the overall escape interval of the pacemaker, as well as various refractory, blanking, and other timing windows (shown in FIG. 3) for controlling the operation of the peripheral components within input-/output circuit 132.

Digital controller/timer circuit 132 is coupled to sense amplifiers 146, 146' for receiving amplified and processed R-wave and P-wave signals picked up from ventricular and atrial electrodes 103, 105 and 109, 111 through leads 102, 106 and capacitors 108, 107, respectively, near-field electrical activity of the patient's heart 104. Sense amplifiers 146, 146' produce ventricular sense (VS) and atrial sense (AS) event signals for re-setting the escape interval timers within circuit 132. Output pulse generators 150, 150' provide the ventricular and atrial pacing stimuli to the patient's heart 104 in response to VP and AP trigger signals developed by digital controller/timer circuit 132 each time the A—A and V—V lower rate escape interval times out, or an externally transmitted pacing command has been received, or in response to other stored commands as is well known in the pacing art.

In a preferred embodiment of the present invention, pacemaker 100 is capable of operating in various non-rate-responsive modes which include AAI, ADD, AAT, VVI, VOO, and VVT, as well as corresponding rate responsive modes of AAIR, AVOR, AATR, VVIR, VOOR, and VVTR or may be configured as a dual chamber DDD/DDDR pacing system, in certain embodiments described hereafter. A further example of circuitry suitable for implementing this portion of the pacer can be found in U.S. Pat. Nos. 4,596,251 and 4,253,466, which are incorporated herein by reference.

In the context of the present invention, the CSI sensor signal picked up from the blood oxygen and/or pressure or flow sensor used to detect cardiac muscle stress is first processed in block 154, and then mathematically processed in circuit 132, to develop a control signal that is employed to select the ratio of paired and coupled pacing events to total pace and sense events, or to control the paired and triggered pacing interval.

In the preferred embodiments employing the CPI sensor for correlating cardiac output to demand for oxygenated blood, it may be coupled to a processing-/amplifying circuit 152 for receiving, amplifying, and processing sensor output signals from one of the aforementioned CPI sensors.

In the context of the present invention, it would also be desirable to develop stored data bases for correlating the output signals of both sensors reflecting the level of the patient's activity to the oxygen or pressure or flow sensor output signals for subsequent telemetry out and analysis. For example, the first sensor's oxygen, pressure, or flow signals having values persisting at an extreme of the expected range may be correlated to the second sensor's signals to make certain that the sensors are operating correctly or to relate sensor-detected cardiac stress to cardiac output at then prevailing ratios of paired and coupled pace events to non-paired and coupled events. Thus, the sensors may provide functions and data ancillary to the principal function and data collection attendant to regulating the ratio of paired or coupled stimulation to total sensed or paced events.

Figure 3:
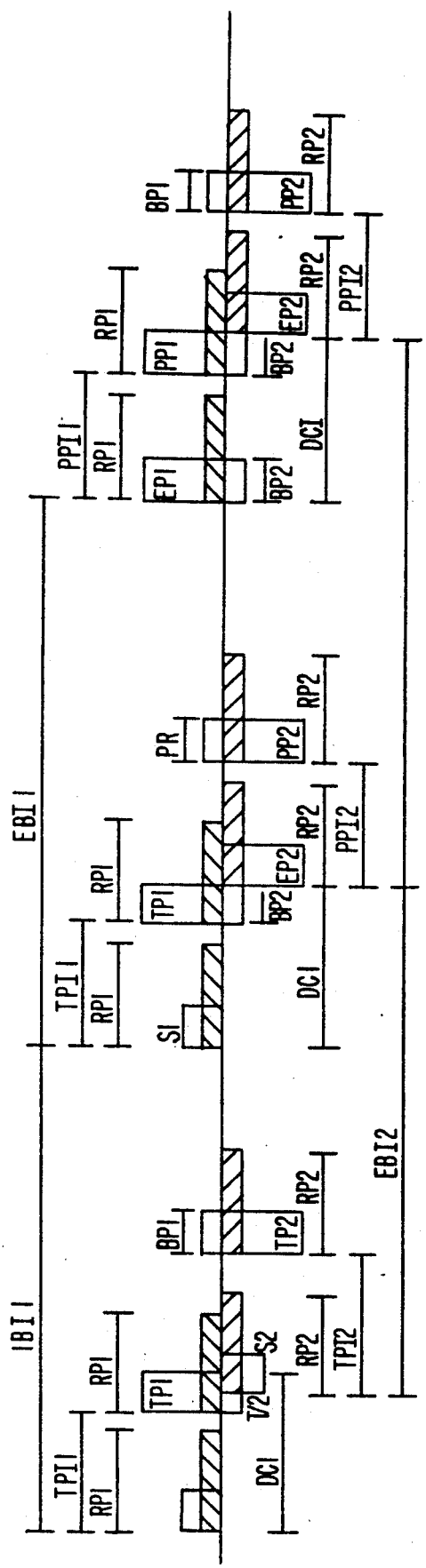
FIG. 3 is a timing diagram of atrial and ventricular stimulation and sensed event related intervals in the dual chamber pacing system of FIG. 2.

A timing diagram of the system of FIG. 2 is depicted in FIG. 3 where atrial activity and intervals are depicted above the horizontal time line and ventricular activity and intervals are depicted below the line. A set of operating modes and programmable parameters for the pacing system and the timing diagram follows. In this listing, channel 1 refers to the atrial channel and channel 2 refers to the ventricular channel for all listed parameters.

In reference to FIG. 3, the pacemaker operates at a basic escape beat interval (EBI) that may be set by a rate response algorithm or be programmed. The pulse characteristics (amplitude and width) of escape pulses, (EP1 and EP2) should be programmable. A "paired pulse" or a "triggered pulse" (or coupled pulse) should be delivered a programmable interval (PPI) or (TPI), respectively, after the delivery of an escape pulse (in this embodiment, the intervals do not vary as a function of the cardiac stress sensor output signal). The pulse width and amplitude of the paired pulse should be programmable. If dual chamber operation of the pacemaker is selected, a dual chamber interval (AV Interval) timer should begin at the time of a channel 1 sensed event (S1) or delivery of an escape pulse (EPI) in Channel 1. When this timer times out, the escape pulse (EP2) should be delivered in Channel 2. A blanking period (BP1) should be enabled in Channel 1 whenever a Channel 2 stimulus pulse is delivered, and a blanking period (BP2) should be enabled in Channel 2 whenever a Channel 1 stimulus is delivered. The blanking period may overlap the refractory periods and provide similar functions.

The programmable characteristics for the system of FIGS. 2 and 3 as set forth below are: min, max, increment, nominal.

S1 SENSED EVENT, CHANNEL 1. When a sensed event occurs on this channel, the following occurs:
EBI1 Timer resets, TPI1 Timer resets,
RP1 Timer resets,
DCI Timer resets (if DC FLAG is YES)
The sensitivity of this channel is programmable: 0.01, 5.0, 0.01, 0.25 (v)

TP1: TRIGGERED PULSE, CHANNEL 1. The triggered pulse is the pulse delivered following a sensed event. The triggered pulse follows the sensed event by the TPI1 interval. The triggered pulse is only delivered if the CH1 FLAG is YES. When a TP1 pulse is delivered, the following occurs:
RP1 Timer resets,
BP2 Timer resets,
TP1 characteristics are programmable:
PW: 0.01, 5.00, 0.01, 0.50 (ms)
PA: 0.10, 10.0, 0.10, 1.00 (v)

TPI1: TRIGGERED PULSE INTERVAL, CHANNEL 1. The triggered pulse interval is the time from a sensed event to delivery of a triggered pulse, TP1. The triggered pulse interval begins at the time of detection of a sensed event, S1. It is reset by detection of another sensed event before the TPI1 interval expires and the triggered pulse is delivered.

EP1: ESCAPE PULSE, CHANNEL 1. The escape pulse is the pulse delivered following time-out of the escape interval EBI1. When an EP1 pulse is delivered, the following occurs:
EBI1 Timer resets,
TPI1 Timer resets,
RP1 Timer resets,
BP1 Timer resets,
DCI Timer resets (if DC FLAG is YES)
EP1 characteristics are programmable:
PW: 0.01, 5.00, 0.01, 0.50 (ms)
PA: 0.10, 10.0, 0.10, 1.00 (v)

PP1: PAIRED PULSE, CHANNEL 1. The paired pulse delivered following an escape pulse. The paired pulse follows the escape pulse by the PPI1 interval. The paired pulse is only delivered if the CH1 FLA YES. When a PP1 pulse is delivered, the following occurs:
RP1 Timer resets,
BP2 Timer resets,
PP1 characteristics are programmable:
PW: 0.01, 5.00, 0.01, 0.50 (ms)
PA: 0.10, 10.0, 0.10, 1.00 (V)

PPI1: PAIRED PULSE INTERVAL, CHANNEL 1. The paired pulse interval is the time from delivery of the escape pulse, EP1, to the delivery of the paired pulse, PP1. The paired pulse interval begins at the time of delivery of the EP1. It is reset by detection of a sensed event before the PPI1 interval expires and the paired pulse is delivered, or at the actual time of delivery of PP1.

RP1: REFRACTORY PERIOD, CHANNEL 1. The refractory period is the period following a sensed event or stimulus pulse during which no additional sensed event can occur. The timer for this period starts with: a sensed event, S1; a triggered pulse, TP1; an escape pulse, EP1; or a paired pulse, PP1.
RP1 is programmable: 0.00, 500, 10.0, 100 (ms)

BP1: BLANKING PERIOD, CHANNEL 1. The blanking period is the time during which a sensed event cannot occur (sense amp blanked). It starts at the time of delivery of a triggered pulse on Channel 2, TP2, an escape pulse on Channel 2, EP2, or a paired pulse on Channel 2, PP2. The BP1 is irrelevant if Channel 2 is not being used for stimulation.
The BP1 interval is programmable: 0.00, 20.0, 0.10, 10.0 (ms)

IBI1: INTRINSIC BEAT INTERVAL, CHANNEL 1. This interval is the time between intrinsic events. It is not timed by the device.

EBI1: ESCAPE BEAT INTERVAL, CHANNEL 1. The escape beat interval is the basic, maximum allowable interval between Channel 1 events. The escape beat interval timer is reset by the detection of a sensed event, S1, or by delivery of an escape pulse, EP1. The escape beat interval is computed as 60,000/basic escape rate. The basic escape rate is programmable: 30, 250, 5, 70 (bpm)

CHANNEL 2 FEATURES.

S2: SENSED EVENT, CHANNEL 2. When a sensed event occurs on this channel, the following occurs:
EBI2 Timer resets,
TPI2 Timer resets,
RP2 Timer resets,
The sensitivity of this channel is programmable: 0.01, 5.0, 0.01, 0.25 (v)

TP2: TRIGGERED PULSE, CHANNEL 2. The triggered pulse is the pulse delivered following a sensed event. The triggered pulse follows the sensed event by the TPI2 interval. The triggered pulse is only delivered if the CH2 FLAG is YES. When a TP2 pulse is delivered, the following occurs:
RP2 Timer resets,
BP1 Timer resets,
TP2 characteristics are programmable:
PW: 0.01, 5.00, 0.01, 0.50 (ms)
PA: 0.10, 10.0, 0.10, 1.00 (V)

TPI2: TRIGGERED PULSE INTERVAL, CHANNEL 2. The triggered pulse interval is the time from a sensed event to delivery of a triggered pulse, TP2. The triggered pulse interval begins at the time of detection of a sensed event, S2. It is reset by detection of another sensed event before the TPI2 interval expires and the triggered pulse is delivered.

EP2: ESCAPE PULSE, CHANNEL 2. The escape pulse is the pulse delivered following time-out of the escape interval EVI1. When an EP1 pulse is delivered, the following occurs:
EBI2 Timer resets,
TPI2 Timer resets,
RP2 Timer resets,
BP1 Timer resets,
EP2 characteristics are programmable:
PW: 0.01, 5.00, 0.01, 0.50 (ms)
PA: 0.10, 10.0, 0.10, 1.00 (v)

PP2: PAIRED PULSE, CHANNEL 2. The paired pulse is the pulse delivered following an escape pulse. The paired pulse follows the escape pulse by the PPI2 interval. The paired pulse is only delivered if the CH2 FLAG is YES. When a PP2 pulse is delivered, the following occurs:
RP2 Timer resets,
BP1 Timer resets,
PP2 characteristics are programmable:
PW: 0.01, 5.00, 0.01, 0.50 (ms)
PA: 0.10, 10.0, 0.10, 1.00 (v)

PPI2: PAIRED PULSE INTERVAL, CHANNEL 2. The paired pulse interval is the time from delivery of the escape pulse, EP2, to the delivery of the paired pulse, PP2. The paired pulse interval begins at the time of delivery of the EP2. It is reset by detection of a sensed event before the PPI1 interval expires and the paired pulse is delivered, or at the actual time of delivery of PP2.

RP2: REFRACTORY PERIOD, CHANNEL 2. The refractory period is the period following a sensed event or stimulus pulse during which no additional sensed event can occur. The timer for this period starts with: a sensed event, S2; a triggered pulse, TP2; an escape pulse, EP2; or a paired pulse, PP2.

RP2 is programmable: 0.00, 500, 10.0, 100 (ms)

BP2: BLANKING PERIOD, CHANNEL 2. The blanking period is the time during which a sensed event cannot occur (sense amp blanked). It starts at the time of delivery of a triggered pulse on Channel 2, TP1, an escape pulse on Channel 1, EP1, or a paired pulse on Channel 1, PP1. The BP2 is irrelevant if Channel 1 is not being used for stimulation.

The BP2 interval is programmable: 0.00, 20.0, 0.10, 10.0 (ms)

IBI2: INTRINSIC BEAT INTERVAL, CHANNEL 2. This interval is the time between intrinsic events. It is not timed by the device.

EBI2: ESCAPE BEAT INTERVAL, CHANNEL 2. The escape beat interval is the basic, maximum allowable interval between channel 1 events. The escape beat interval timer is reset by the detection of a sensed event, S1, or by delivery of an escape pulse, EP1. The escape beat interval is computed as 60,000/basic escape rate.

The basic escape rate is programmable: 30, 250, 5, 70 (bpm)

One application of the system as described in conjunction with the preferred embodiments is the electro-augmentation of the contraction of the atrial chambers due to PESP stimulation of the atria to overcome the inability of the atria to contract forcefully enough to fill ventricles that have been thickened by congestive heart failure for subsequent expulsion of blood into the arterial systems. Patients with congestive heart failure often suffer cardiac output insufficiency due to the insufficient filling of the ventricle. To treat this condition, it is proposed to apply paired and triggered stimulation pulses PP1, TP1, to the right atrium with a coupling interval TPI1, PPI1 that is long enough to trigger atrial PESP, but so short as to not be conducted to the ventricle and trigger ventricular PESP. In this fashion, the atrial filling of the ventricles will be augmented while the oxygen uptake demand is not increased as significantly as it is in ventricular PESP. The CSI sensor located in the coronary sinus will still reflect a degree of oxygen depletion due to atrial PESP that can be employed to modulate the coupling interval and/or the ratio of paired and coupled atrial stimulation P—P intervals to total P—P intervals.

In another application, it is proposed to also apply the paired and triggered stimulation pulses PP2, TP2, to the right ventricle with or without atrial stimulation pulses PP1, TP1, in those patients where electrophysiologic testing of the application of such stimulation indicates that synchronous atrial and ventricular PESP effects provide beneficial increases in cardiac output that can be effectively modulated by the sensor output signal and algorithm to avoid angina and other cardiovascular system stress.

In these applications, and in the earlier described application, there is a possibility that the intervals PPI1, PPI2 and TPI1, TPI2, are inappropriate and ineffective for the realization of PESP effects. Thus, it is also proposed that a burst of "n" spaced apart pacing pulses PP1$_n$, PP2$_n$, TP1$_n$, TP2$_n$ be generated and applied bracketing the end of the paired and triggered intervals to assure that at least one of the pulses is effective. Moreover, it is contemplated that the algorithm used may also include a self-checking feature that determines the effective atrial and ventricular refractory periods in the manner described in U.S. Pat. No. 4,280,502, incorporated herein by reference. Moreover, the CSI sensor output signal reflecting increases in oxygen uptake and/or the CPI sensor output signal reflecting ventricular or arterial pressure reflecting PESP performance may be sampled in a test mode of a series of paired and triggered intervals to identify the effective coupling intervals for subsequent clinical use.

In the context of the dual chamber pacing system of FIG. 2, it is desirable to employ paired or triggered atrial stimulation under physician observation and to detect whether it elicits PESP in the ventricle. In this connection, a ventricular EGM may be detected by sense amplifier 146 and telemetered out as paired or coupled atrial stimulation is commanded in a temporary test mode. If ventricular PESP can be observed by atrial stimulation at certain intervals, then the pacemaker may be programmed to so operate with those intervals. Alternatively, the detected intervals which do not elicit ventricular PESP may be used to program the device to provide atrial augmentation only.

If the PESP effect from atrial stimulation cannot be elicited in the ventricle, then the pacemaker may be programmed to provide periodic atrial and ventricular sequential paired and triggered stimulation (again initially in a temporary test mode) to gain the benefits of periodic PESP stimulation. In either case, the ratio of escape intervals terminated by paired or triggered pacing to total escape intervals is under the control of the sensor control algorithm.

As mentioned above, paired and triggered stimulation also effectively reduces the spontaneous heart rate and has been used extensively in anti-tachyarrhythmia devices. Patients who would benefit from PESP may also be at risk experiencing spontaneous or stimulation-triggered malignant arrhythmias. Consequently, it is desirable to provide backup anti-tachyarrhythmia stimulation therapies. Conversely, it is desirable to expand the uses of such anti-tachyarrhythmia control devices to provide a combination of potential therapies to patients suffering from cardiac insufficiency as well as instability.

Figure 4:
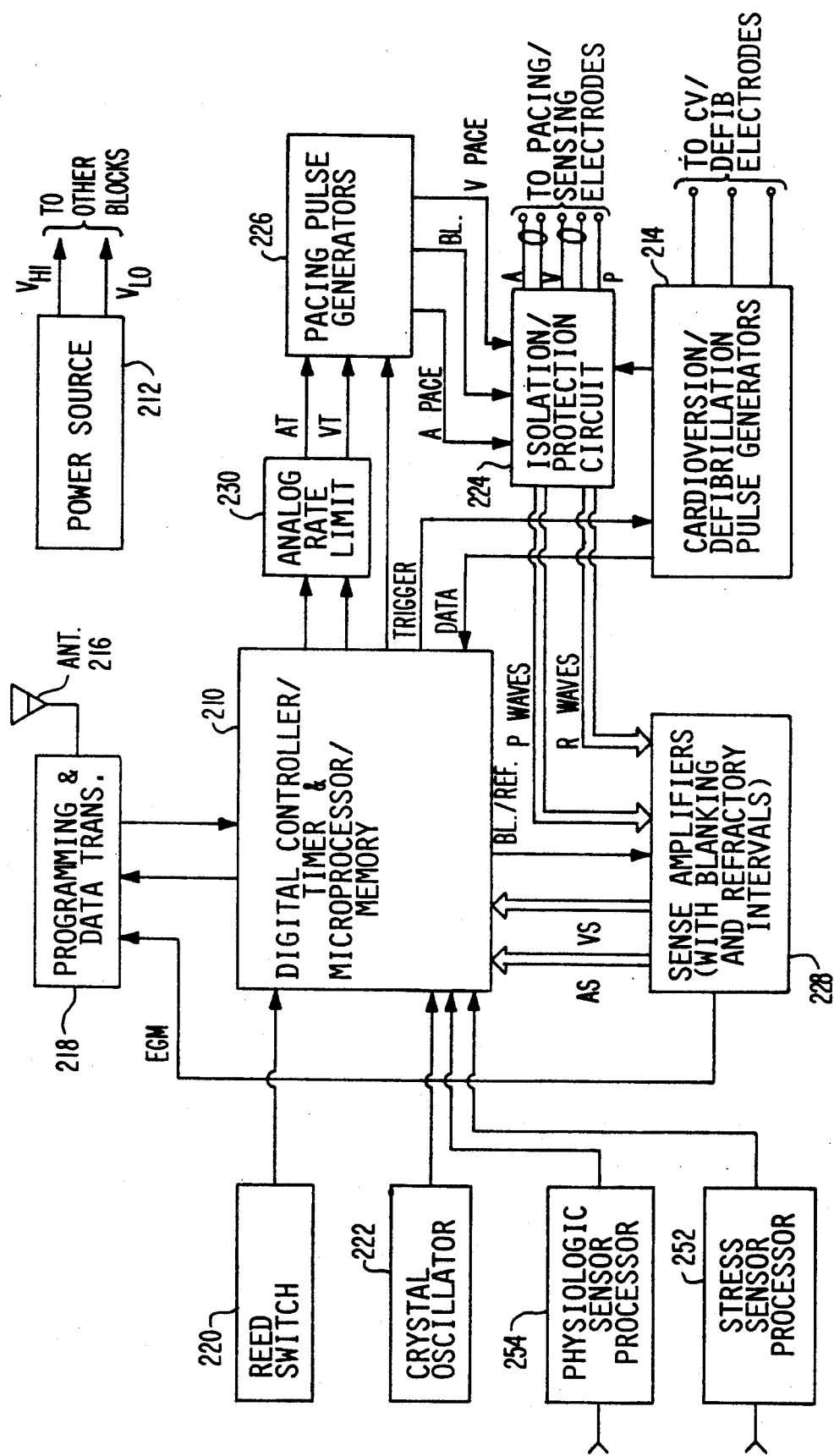
FIG. 4 is a simplified block diagram of a pacemaker-cardioverter-defibrillator system in which the PESP stimulation system of the present invention may be implemented.

Reference is now made to FIG. 4 which depicts a block diagram of the major components of automatic implantable device for detecting and treating brady and tachyarrhythmias that the system of the present invention could be incorporated in. It is contemplated that such a device would be implemented in analog and digital microcircuits under the control of a central microprocessor/memory block 210 powered by high (for cardioversion and defibrillation) and low (for the remaining circuitry on pacing therapies) power sources in block 212. The high power pulse generator block 214 would include the cardioversion/defibrillation pulse generator circuitry coupled by output terminals to two or more cardioversion/defibrillation electrodes to apply synchronized cardioversion or unsynchronized defibrillation shocks to the electrodes situated in or about the heart in a manner well known in the art.

It is contemplated that the implantable device depicted in FIG. 4 would function under the control of a resident operating program or software retained in memory within the microprocessor/memory block 210 and would be programmable by an external programmer/receiver (not illustrated in FIG. 4) communicating with the implanted device by radio frequency energy received or transmitted by antenna 216 under the control of the programming and data transmission block 218 and reed switch 220 which is responsive to an external magnet. The programming and data transmitting block 218 would be capable of receiving programming instructions of the type listed above and directing them to the memory within microprocessor/memory block 210, as well as transmitting data stored within the memory block 210, as well as an electrogram representing the patient's atrial and ventricular activity in a manner well known in the pacing art.

The timing of all processing functions, including the determination of atrial and ventricular cycle lengths, is controlled by system clocks within microprocessor/memory 210, driven by crystal oscillator 222 in a manner well known in the prior art of implantable digital pacemakers.

The cardiac signal processing blocks of FIG. 4 include the isolation/protection or interface block 224, which operates to direct atrial and ventricular pacing stimuli from the pacing pulse generator block 226 to respective atrial and ventricular output terminals, which in turn are coupled through the pacing leads to the bipolar pacing electrodes situated in or near the atrium and ventricle of the heart as shown in FIG. 2. In addition, the interface 224 (when unblanked) couples the atrial and ventricular electrograms to the sense amplifier block 228. Interface 224 is blanked or prevented from passing any signals picked up on the atrial and ventricular pacing/sensing electrodes to the sense amplifier block 228 during short blanking intervals following the delivery of an atrial or ventricular pacing stimulus in a fashion well known in the pacing art.

The microprocessor/memory 210 responds to atrial (A) and ventricular (V) sense (S) signals by generating appropriate atrial and ventricular refractory and blanking intervals which are in turn applied to the sense amplifier block 221 during certain windows of time following each respective AS and VS signal in a fashion well known in the pacing art.

Furthermore, the interface 224 disconnects or shorts out the pacing/sensing electrodes during the delivery and for a short period after the delivery of a cardioversion/defibrillation shock by application of a control signal to the interface 224 by the cardioversion/defibrillation pulse generator block 214 as is known in the art.

The P-wave and R-wave signals transmitted through the interface 224 to the sense amplifiers 228 are amplified and shaped to generate the atrial and ventricular sense event signals AS and VS, respectively, which are conducted to microprocessor/memory 210 to derive the atrial and ventricular cycle lengths, the AV delay interval, the paired and coupled pace intervals, and other intervals and parameters described hereinbefore to perform the inventive functions of the device. The further signal from the physiologic sensor signal processor block 254, representative of oxygen saturation, and/or blood pressure, and/or blood flow, is also applied to the microprocessor/memory 210 to control the bradyarrhythmia pacing rate in the DDDR or other rate-responsive mode of operation, to augment detection of tachyarrhythmias, and to control the ratio of paired and coupled pacing to total pacing.

It is contemplated that the system depicted in FIG. 4 may be programmed to operate in any of the known bradycardia single or dual chamber pacing modes. The signal from the physiologic sensor may be employed to modify the atrial and ventricular escape intervals to allow for a certain range of atrial and ventricular pacing depending upon the level of the patient's activity in a fashion well known in the bradycardia pacing art. Suffice it to say, that atrial and ventricular escape intervals established in memory are compared against the atrial and ventricular cycle lengths encountered in the patient and, if a bradycardia condition exists, the microprocessor/memory 210 applies atrial and ventricular pace trigger signals AT and VT through analog rate limiter block 230 to the pacing pulse generator 226 which responds by developing the respective A pace and V pace signals. Analog rate limiter 230 operates to limit atrial and ventricular pacing rates to a safe high rate and effect an appropriate upper rate behavior in the event that the spontaneous atrial rate exceeds the programmed upper rate limit, as is described above, in relation to the second embodiment of the invention.

Figure 5:
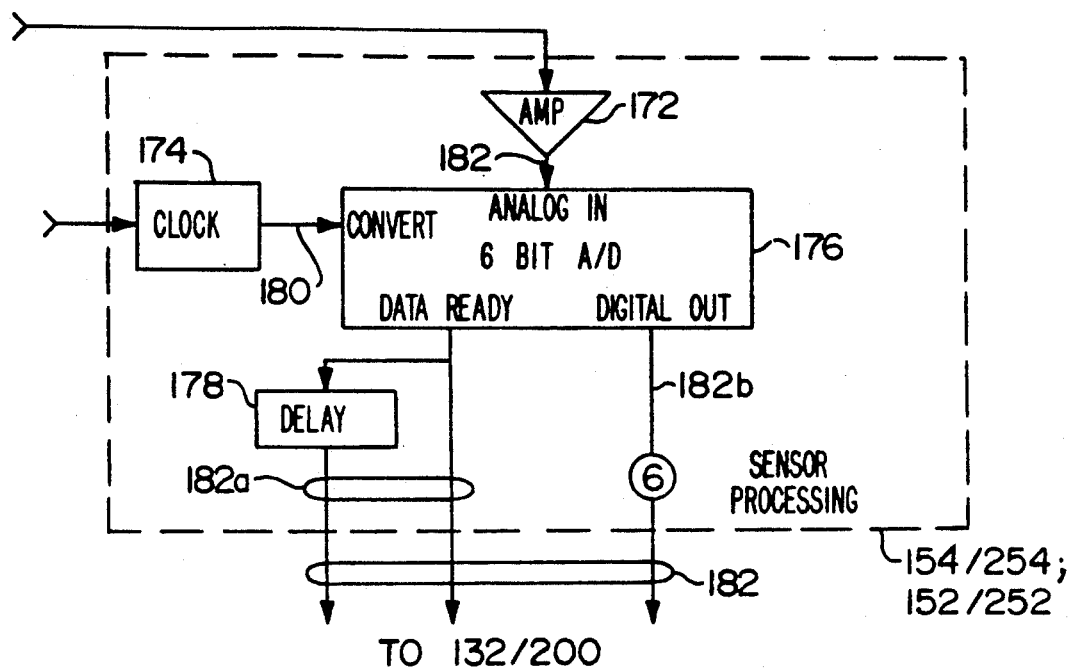
FIG. 5 is a schematic diagram of sensor processing logic for providing the cardiac stress and performance feedback control signals for controlling application of PESP stimulation in the embodiments of FIGS. 1 to 4.

Turning now to FIG. 5, a detailed schematic view of the stress and sensor processing blocks 18/154/254 and 34/152/252 of the preceding figures is shown which corresponds in general to FIG. 4 of the incorporated '807 patent. The analog sensor information received from the oxygen sensor, for example, is simply a signal having a voltage that is proportional to the percentage of concentration of molecular oxygen in the coronary venous blood in or near the coronary sinus. Amplifier 172 processes the analog signal and scales it for input to six bit A/D converter 176 via line 182. The processed analog signal is converted by a six-bit A/D converter 176 into a digital signal, which is transmitted via cable to a six-bit latch (not shown). The data ready output signal is supplied via one conductor 182a of cable 182 to clear six-bit latch 160. The data ready signal is delayed by delay 178 and sent via the other conductor of cable 182a to enable the six-bit data into six-bit latch 160. Clock 174 supplies the convert signal to six-bit A/D converter 176. The clock 174 may be triggered periodically with the delivery of paired or triggered stimulation as described hereafter in conjunction with FIGS. 6 and 7. Thus, the incoming analog signal is converted to a six-bit data signal, which may be employed in the systems of FIGS. 1 to 4 in conjunction with a system of the type depicted in FIG. 6, to control the ratio of delivery of the paired or triggered pulse to the number successive sensed or stimulated events that reset the A—A or V—V intervals.

Figure 6:
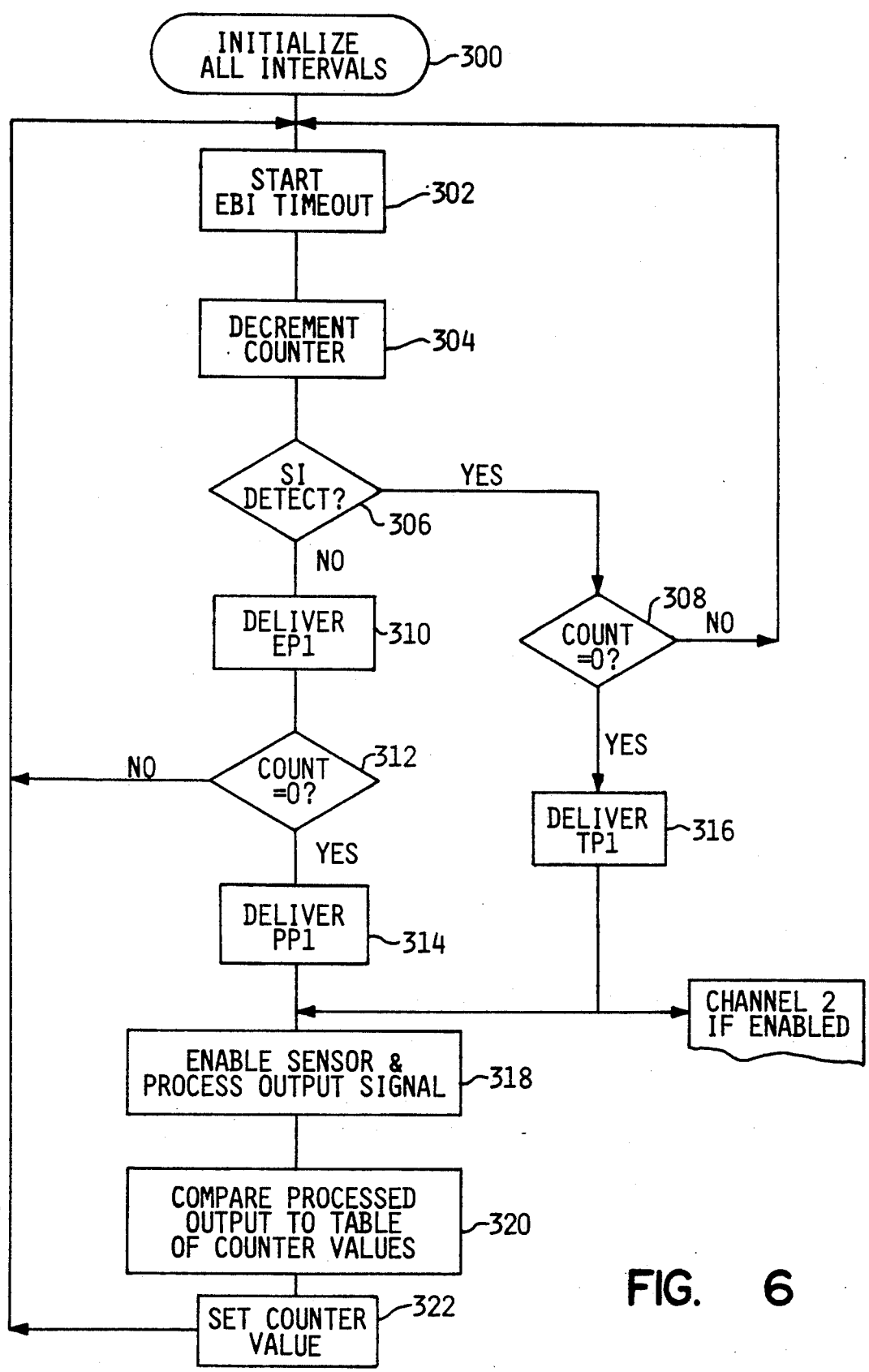
FIG. 6 is a flow chart of an algorithm for providing atrial and/or ventricular stimulation with triggered PESP stimulation and physiologic sensor feedback control that may be implemented in any of the embodiments of FIGS. 1 to 4.

Turning now to FIG. 6, a simplified algorithm of setting the ratio of paired and coupled pacing pulses to total heart beats at the pacing rate is depicted for use in conjunction with any of the preferred embodiments described above. In FIG. 6, at block 300, the intervals are those that are specified above for at least a single chamber pacing system, such as the channel 1 or atrial pacing system. At block 302, the EB1 time-out counter is started. Simultaneously, the counter is decremented in block 304 from its preceding count, which likewise was initiated in block 300. At block 308, the algorithm looks for the detection of a sensed event in channel 1 during the time-out of the EB1 escape interval, and if a signal S1 is detected before that time-out occurs, then the contents of the counter are examined in block 308. If the count in block 308 is other than zero, then the algorithm looks back to start the EB1 escape interval timeout in block 302.

If the signal S1 is not detected before the interval EB1 times out, then the pace pulse EP1 is delivered in block 310. At the same time, the count is again examined in block 312, and if it is not at zero, then the program loops back again to block 304.

If in either case the count in counter zero does equal zero, then either a paired or coupled pulse PP1, TP1 is delivered as indicated in blocks 314, 316.

At a suitable time after the delivery of the paired or coupled pulse, the sensor clock 174 of FIG. 5 is enabled in block 318 to sample and convert the oxygen sensor value in a manner described in the incorporated U.S. Pat. Nos. 4,467,807 to Bornzin and 4,570,495 to Moore et al. After the analog sensor signal is converted to a digital value, it is compared in block 320 to a table of counter values in a look-up chart based upon the relationships depicted in FIG. 6 in regard to the prevailing heart rate to develop a number that the counter is set to in block 322. After the counter in block 322 is set, the program loops back to start the EB1 time-out in block 302.

Thereafter, as the escape intervals are timed out, the counter is decremented until it again reaches zero, whereupon a paired or coupled pacing pulse is delivered. The algorithm depicted in FIG. 6 would be duplicated essentially for a ventricular channel, or channel 2, if it is enabled in any of the above-mentioned systems.

Figure 7:
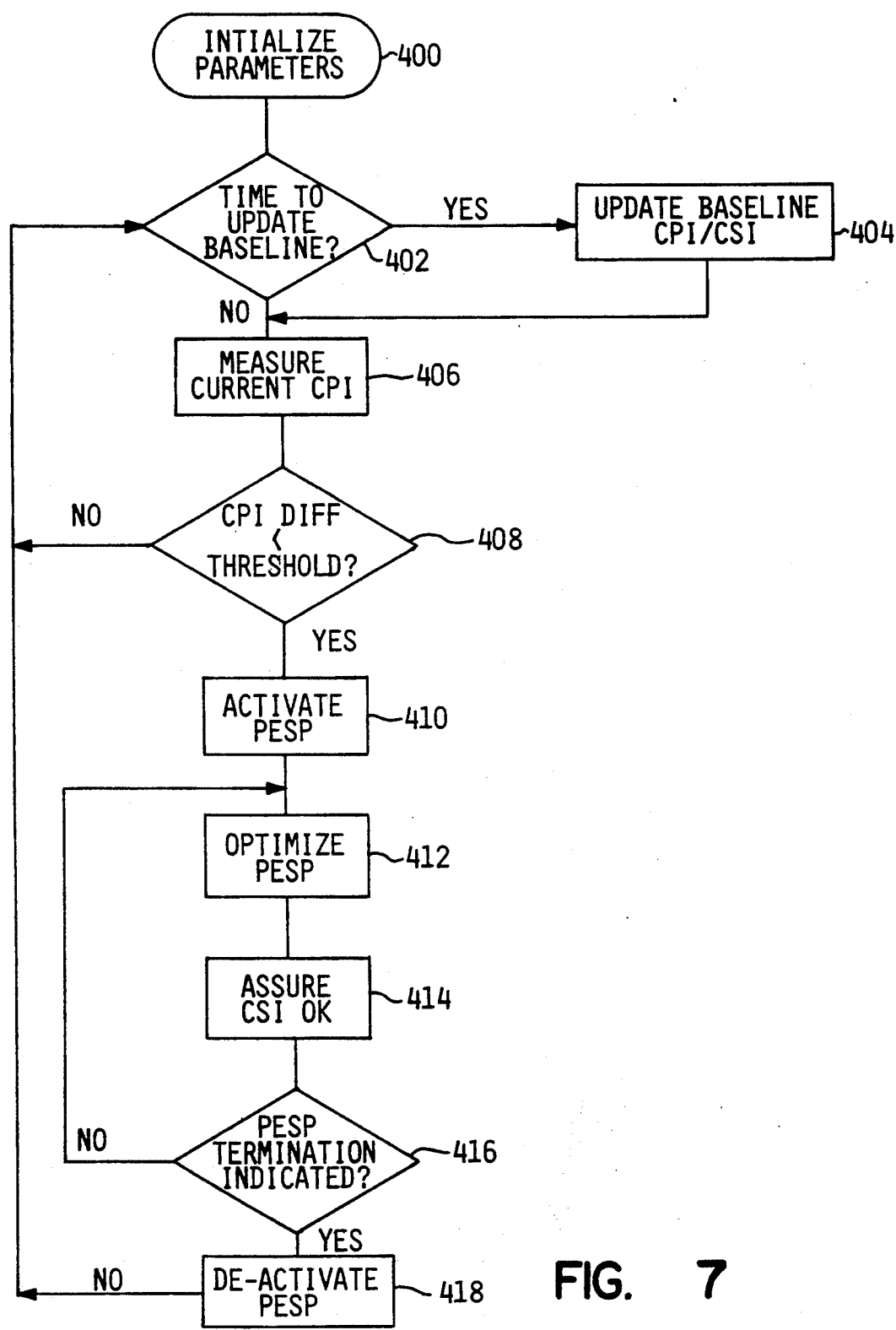
FIG. 7 is a flow chart of an algorithm for providing PESP stimulation based on cardiac stress and performance feedback signals that may be implanted with the FIG. 6 algorithm in any of the embodiments.

FIG. 7 depicts a further flow chart of the procedure for implementing the sensor controlled PESP feature in a cardiac stimulator.

The intended implementation of a sensor-controlled PESP feature requires that there be baseline data available from each of the controller variables representing a long-term average value for the cardiac performance index (CPI) and for the cardiac stress index (CSI). The baseline values will serve as reference values against which current, short-term samples of the variable can be checked. The baseline measurements can be made continuously, as long as PESP is not activated, or periodically when the baseline timer times out (block 402); for continuous operation this timer would be set very short, at or virtually to zero.

When the PESP option is first turned on within the stimulator, all required parameters for the algorithm are initialized at block 400.

Block 404 is the actual block where the baseline or long-term averages for CPI and CSI are acquired and computed. The long-term averages may be running n-sample averages, running n-time averages, discrete n-sample averages, or discrete n-time averages.

In block 406, the current value for the CPI parameter is measured. The current value may be a single sample or a short-term average of the CPI variable. The short-term average may be a running n-sample average, a running n-time average, a discrete n-sample average, or a discrete n-time average.

In block 408, a comparison is made between the current CPI value and the baseline CPI value. If the difference is greater than a preset level, the decision is made to activate the PESP feature. If not, the feature remains off, and the system continues back to block 402. The threshold may be a preset, absolute difference between the current and baseline CPI values, or a preset percentage difference between the current and baseline CPI values.

At block 410, the PESP feature is activated, and coupled/paired stimulation begins at the initial levels for triggered pulse interval (TPI) and paired pulse interval (PPI). The initial TPI and PPI ratio is 1:1; that is every beat has PESP. The basic pacing rate is at the initial escape beat interval, EBI.

Block 412 executes the logic for optimizing the PESP feature based on the CPI variable. CPI optimization may operate based on one or more CPI variables simultaneously. Optimization first seeks a minimal heart rate. If the patient's intrinsic beat interval (IBI) is greater than the EBI, i.e., the patient is being paced regularly at the EBI, then the EBI is incremented to achieve a lower heart rate. This continues until the maximum EBI is reached or the IBI becomes less than the EBI (tracking of the intrinsic rate is occurring), or until poor or diminished values for CPI are determined. Optimization of EBI is repeated following changes in TPI/PPI or changes in TPI/PPI Ratio (see below). Optimization of EBI also occurs periodically, after the EBI optimization timer times out, even if no change to the TPI/PPI or the TPI/PPI ratio has occurred.

Next, optimization of the extrastimuli coupling interval is done. With extrastimuli at the TPI/PPI coupling intervals, the new, current value of the CPI variable is checked to assure CPI is improved. A preselected increment in the pulse coupling interval (TPI/PPI) is generated periodically, at preselected intervals (typically a few seconds), and the CPI variable is again checked to assure CPI improvement. This process is continued until further increments in coupling interval provide poor or diminished improvement in the CPI variable.

If the TPI/PPI coupling interval has been adjusted by the CSI optimization block (see below), then the TPI/PPI coupling interval will now be shortened by one increment to attempt to get back to the TPI/PPI which provided the optimum CPI. Note that this represents an optimization process, where the TPI/PPI is set to optimize CPI, then adjusted to optimize CSI, then adjusted back by the CPI optimization scheme, etc., until the "operating point" is reached whereby both features are satisfied.

As stated earlier, CPI variables are those measured hemodynamic variables which are indicators of cardiac performance such as systemic arterial pressure, pulmonary arterial pressure, mixed venous oxygen saturation, systemic or pulmonary flow and right or left ventricular pressure or dP/dt max. As noted above, the current value of the CPI variable may be a single sample or a short-term average of the CPI variable; the average may be a running n-sample average, a running n-time average, a discrete n-sample average, or a discrete n-time average.

Turning to block 414, it executes the logic for assuring that CPI optimization has not overly stressed the heart as indicated by the cardiac stress index, CSI. CSI assessment may operate based on one or more CSI variables simultaneously. The CSI assessment, ideally, operates continuously when the PESP feature is activated, although it may also be inactivated so that CPI optimization operates without CSI checking. While the inactivation of CSI assessment might place the heart at greater risk of becoming hypoxic in some patients, this might not occur in patients in whom PESP is being used but who are known to have normal or adequate coronary flow reserve. The CSI assessment may operate on a somewhat slower time scale, if TPI/PPI coupling intervals are constant (i.e., the CPI optimization feature has stabilized), or it may operate on a faster time scale (continuously) if the TPI/PPI coupling intervals are varying frequently. CSI checking compares changes in the CSI variable to assure the variable remains within a preselected acceptable range. This range may be preselected as an absolute change in the CSI variable from baseline, or may operate as a preselected percentage change in the CSI variable compared to baseline. Similarly to the CPI variable, the current value of the CSI variable may be a single sample or a short-term average of the CSI variable; the average may be a running n-sample average, a running n-time average, a discrete n-sample average, or a discrete n-time average.

If it happens that the TPI/PPI required to provide an improved cardiac performance, as measured by the CPI variable in block 412, also produces an unacceptable stress to the heart, as measured by the CSI variable in this block, then adjustment of the TPI/PPI Ratio is instituted so that every nth heart beat has the extrastimulus disabled to effectively reduce the number of extrastimuli; this reduces the work required by the heart and will result in an improvement in the CSI variable. The TPI/PPI Ratio is adjusted in preselected increments (see FIGS. 8A and B) until the frequency of potentiated (or "electro-augmented") beats gets the CSI variable into the acceptable range. Tests of the effect of the frequency of extrastimuli on CSI are conducted whenever the CSI variable is in the unacceptable range—excess the CSI threshold—or whenever the TPI/PPI Ratio timer, which controls the frequency of this test, times out.

An alternative adjustment to be made to the CSI optimization scheme, is to adjust the TPI/PPI coupling intervals. Coupling intervals longer than the ideal intervals reduce the magnitude of the potentiation effect, but also reduce the work load placed on the heart. Increments in the TPI/PPI coupling interval would be done when the CSI variable is in the unacceptable range, to restore it back to an acceptable level. This adjustment interacts with the PESP optimization adjustment described in block 406 above, so that a TPI/PPI coupling interval is sought by the algorithm which provides the best CPI optimization at an acceptable level of the CSI variable.

Turning to block 416, it describes a routine check feature which is continuously functional while the PESP feature is activated. This check provides several options or conditions under which the PESP feature is deactivated or turned off. As described previously, this feature may be manually deactivated if undue stress (i.e., chest pain) is being detected by a patient. This deactivation would remain permanent, either until the patient is examined again by a health care specialist, who could reset the manual deactivation feature or "temporary" until a reset timer times out, after which the PESP feature would again be allowed to be activated should the CPI check feature (block 408) call for it. The deactivation feature would also be invoked in other conditions, such as the presence of tachycardia. Similarly, if the patient's intrinsic beat interval becomes less than a preselected minimal value, the PESP feature would be deactivated. This form of deactivation could be reset once the patient's heart rate—intrinsic beat interval—returns to the acceptable range. The deactivation feature would also be triggered if the full range of allowable adjustments of the TPI/PPI coupling intervals had been tried and no improvement in the CPI variable was apparent; a timer could again time out to allow re-initiation of the PESP feature. The deactivation feature would also be triggered if no setting of TPI/PPI could be found which kept the CSI variable in the acceptable range; a timer could again time out to allow re-initiation of the PESP feature. Block 418 turns off PESP when indicated in block 416.

Figure 8A:
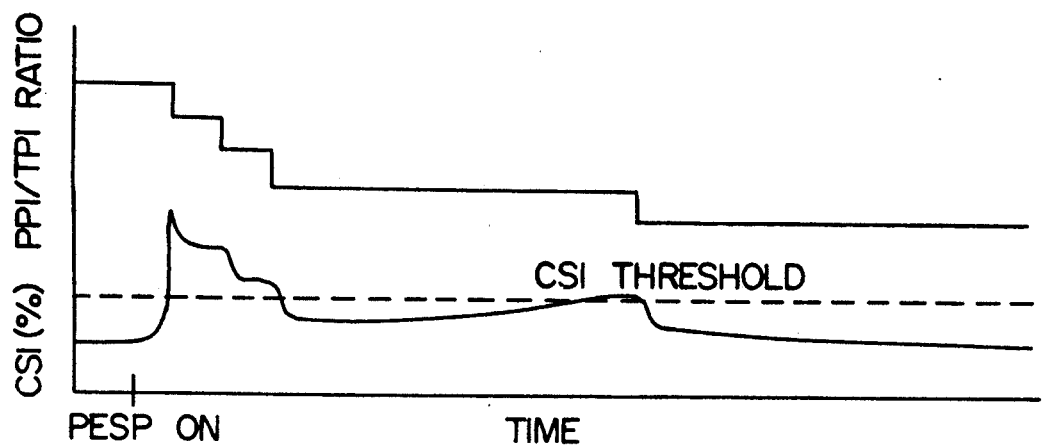
FIG. 8, panels A and B, depict PESP to normal pacing adjustments in response to cardiac stress (CSI).
Figure 8B:
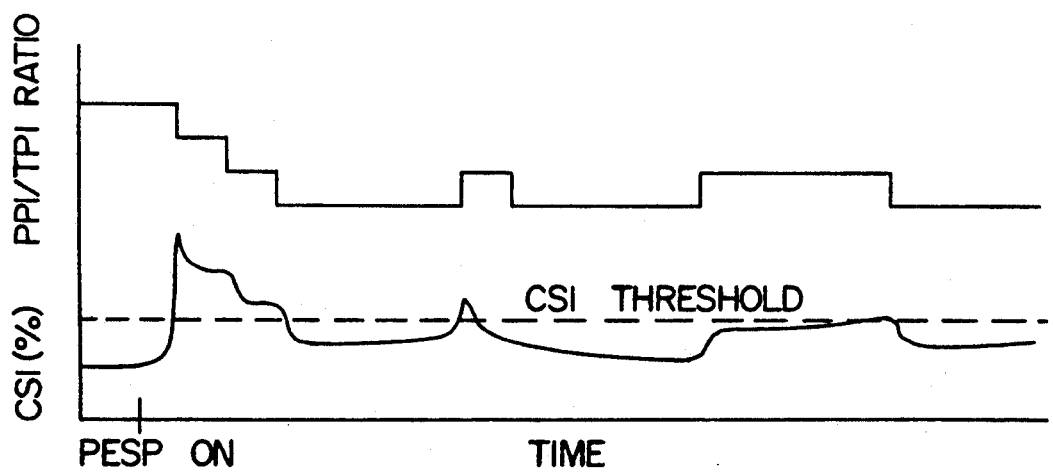

Turning now to FIG. 8, it is a schematic illustration in two panels, A and B, of the behavior of the modes for TPI/PPI Ratio adjustment to provide cardiac protection by assuring the CSI variable is in an acceptable range. Panel A shows the behavior with threshold checking operation. In this case, the CSI variable exceeds the threshold when PESP is activated. The TPI/PPI Ratio is decremented in preselected steps until the CSI comes below the threshold. The TPI/PPI Ratio remains at this level. Later in time, the CSI variable drifts upward, again exceeding the threshold. The TPI/PPI Ratio is again decremented to keep the CSI in the acceptable range.

Panel B of FIG. 8 shows the behavior of the continuous mode of operation. In this case, the TPI/PPI Ratio is decremented at the onset of activation of PESP just as it was in the prior example. Now, however, after the TPI/PPI Ratio timer times out, the TPI/PPI Ratio is again increased to assure the greatest ratio is being used. The subsequent check of CSI shows this ratio again moves the CSI variable into the unacceptable range—above threshold—and the ratio is again decremented. This process would repeat whenever the timer times out.

Further, as technological advances are made, for example, in developing practical small-size, low-cost high voltage components, similar to the advances in the semiconductor field, the principles of the invention may be applied directly to a "universal" implantable device for performing an all-purpose cardiac treatment function for bradyarrhythmia, tachyarrhythmia, and congestive heart failure in their various combinational manifestations.

Accordingly, it is intended that the invention be limited not by the structural or functional elements of the described embodiment, but only as set out in the appended claims.

What is claimed is:

1. A cardiac pacemaker having escape interval timer means for generating a pace event signal at the time-out of an escape interval, natural heart depolarization sensing means for providing a sense event signal upon sensing a heart depolarization, means for resetting said escape interval timer means in response to pace and sense event signals, pulse generator means responsive to a pace event signal for generating a pacing pulse, and means for applying the packing pulse to a heart, further comprising means for selectively providing post-extrasystolic potentiation effects without undue cardiac stress comprising:
    means for causing said pulse generator means to provide a paired packing pulse a paired pulse interval after the occurrence of a pace event signal in order to induce a post-extrasystolic potentiation effect;
    means for detecting a physiologic response resulting from said post-extrasystolic potentiation effect; and
    means responsive to said detecting means for adjusting said selectively providing means to vary a parameter of said paired packing pulses accordingly.

2. The pacemaker of claim 1 wherein said adjusting means comprises means for selectively varying the ratio of paired packing pulses to total packing pulses provided by said pulse generator over a predetermined number of total pacing pulses.

3. The pacemaker of claim 1 wherein said adjusting means comprises means for selectively varying said paired pulse interval to reduce or increase post-extrasystolic effects.

4. The pacemaker of claim 1 wherein said detecting means comprises means for detecting the level of cardiac stress resulting from said post-extrasystolic potentiation effect.

5. The pacemaker of claim 4 wherein said cardiac stress detecting means further comprises means for detecting the level of coronary sinus blood oxygen saturation and means for providing a cardiac stress index signal when the detected level falls below a threshold level indicative of cardiac muscle oxygen deficiency.

6. The pacemaker of claim 1 wherein said detecting means comprises means for detecting the level of cardiac performance resulting from said post-extrasystolic potentiation effect.

7. A method of operating a cardiac pacemaker to provide post-extrasystolic potentiation effect to augment filling of the ventricular chambers of the heart comprising:
sensing atrial depolarizations;
providing pacing pulses on demand to the atrium of the heart;
providing paired and triggered packing pulses timed from immediately preceding packing pulses and sensed atrial depolarizations, respectively, sufficient to effect post-extra-systolic potentiation of the atrium while falling within the refractory period of the ventricle, whereby ventricular filling is augmented by the more vigorous contraction of the atrium;
establishing a ratio of the application of said triggered and paired packing pulses in relation to a total number of packing pulses and sensed atrial depolarizations;
detecting the level of cardiac stress induced by said post-extrasystolic potentiation; and
adjusting the ratio to avoid undue cardiac stress.

8. The method of claim 7 wherein:
said detecting step comprises measuring the cardiac performance of the ejection of blood from the ventricles; and
said adjusting step comprises adjusting the ratio of said paired and triggered packing pulses to total atrial pacing pulses and sensing of atrial depolarizations to maximize cardiac performance while maintaining an acceptable level of cardiac stress.

9. The method of claim 7 wherein the step of measuring cardiac stress further comprises the steps of:
providing a blood oxygen saturation sensor; and
locating said blood oxygen saturation sensor within the coronary sinus of the patient's heart to detect blood oxygen saturation levels that vary with cardiac muscle oxygen uptake.

10. A cardiac pacemaker for providing post-extrasystolic potentiation effect to augment filing of the ventricular chambers of the heart comprising:
means for sensing atrial depolarizations;
means for providing pacing pulses on demand to the atrium of the heart;
means for providing paired and triggered pacing pulses timed from an immediately preceding pacing pulses and sensed atrial depolarizations, respectively, sufficient to effect post-extrasystolic potentiation of the atrium while falling within the refractory period of the ventricle, whereby ventricular filling is augmented by the more vigorous contraction of the atrium;
means for establishing a ratio of the application of said triggered and paired stimulation pulses in relation to a total number of pacing pulses and sensed atrial depolarizations;
means for detecting the level of cardiac stress induced by said post-extrasystolic potentiation; and
means for adjusting said ratio to avoid undue cardiac stress.

11. The pacemaker of claim 10 wherein:
said detecting means comprises means for measuring the cardiac performance of the ejection of blood from the ventricles; and
said adjusting means comprises means for adjusting the ratio of said paired and triggered stimulation pulses to total atrial pacing pulses and sensing of atrial depolarizations to maximize cardiac performance while maintaining an acceptable level of cardiac stress.

12. The pacemaker of claim 10 wherein said means for measuring cardiac stress comprises:
means for providing a blood oxygen saturation sensor; and
means for locating said blood oxygen saturation sensor within the coronary sinus of the patient's heart to detect blood oxygen saturation levels that vary with cardiac muscle oxygen uptake.

13. A method of operating a cardiac pacemaker for providing stimulating pulses to a patient's heart comprising the steps of:
sensing naturally occurring heart signals and generating a sense event signal;
generating pacing stimulating pulses at a minimum pacing rate, by providing each pacing pulse separated by an escape interval corresponding to the pacing rate;
restarting the escape interval in response to a sense event signal;
measuring a physiological parameter;
comparing said measured parameter to predetermined criteria; and
if said measured physiological parameter meets said criteria, generating a further pacing pulse coupled to preceding packing pulse and sense events after a coupling interval shorter than said escape interval to induce post-extrasystolic potentiation.

14. The method of claim 13 further comprising the steps of:
establishing a ratio of the application of said paired and triggered pacing pulses in relation to a predetermined total number of pacing pulses and sensed events;
detecting the level of cardiac stress induced by the paired pacing pulses; and
adjusting the ratio to avoid undue cardiac stress.

15. The method of claim 14 comprising the steps of:
measuring the cardiac performance of the ejection of blood from the patient's heart; and
adjusting the ratio of paired and pacing pulses to total pacing pulses and sense events to maximize cardiac performance while maintaining an acceptable level of cardiac stress.

16. The method of claim 14 wherein the step of detecting cardiac stress comprises the steps of:
providing a blood oxygen saturation sensor; and locating said blood oxygen saturation sensor within the coronary sinus of the patient's heart to detect blood oxygen saturation levels that vary with cardiac muscle oxygen uptake.

17. An atrial-ventricular cardiac pacemaker for providing atrial and ventricular stimulating pulses to the patient's atrium and ventricle at a predetermined rate and atrial-ventricular synchronous relationship in the absence of naturally occurring atrial and ventricular sense events comprising:

atrial sensing means for sensing naturally occurring atrial heart signals and generating an atrial sense event signal in response thereto;

ventricular sensing means for sensing naturally occurring ventricular heart signals and generating a ventricular sense event signal in response thereto;

atrial pulse generating means for generating atrial stimulating pulses at a minimum atrial packing rate, including atrial timing means for providing each atrial stimulating pulse separated by an atrial escape interval corresponding to a pacing rate, and reset means responsive to an atrial sense event signal for resetting said atrial timing means and restarting the atrial escape interval;

ventricular pulse generator means for generate ventricular stimulating pulses at a minimum pacing rate, including ventricular timing means for providing each ventricular stimulating pulse separated by a ventricular escape interval corresponding to the ventricular pacing rate, and reset means responsive to a ventricular sense event signal for resetting said ventricular timing means and restarting the ventricular escape interval;

means for measuring physiological parameters indicative of the level of myocardial requirements for blood oxygen and the level of myocardial effort and for providing a sensor output signal in response thereto; and means responsive to said sensor output signal for periodically and selectively causing said atrial and ventricular pulse generator means to provide a coupled stimulating pulses at predetermined time intervals following preceding atrial and ventricular sense and pace events to induce post-extrasystolic potentiation.

18. The cardiac pacemaker of claim 17 further comprising means for setting said predetermined time intervals to encompass the refractory period of the myocardial tissue.

19. A cardiac pacemaker having escape interval timer means for generating a pace event signal at the time-out of an escape interval, sensing means for providing a sense event signal upon sensing a heart depolarization, means for resetting said escape interval timer means in response to said pace and sense event signals, pulse generator means responsive to pace event signals for generating pacing pulses, and means for applying said pacing pulses to a heart, further comprising means for selectively providing post-extrasystolic potentiation effects without undue cardiac stress comprising:

means for causing said pulse generator means to provide triggered pacing pulses a triggered pulse interval after the occurrence of said sense event signals in order to induce a post-extrasystolic potentiation effect;

means for detecting a physiologic response resulting from said post-extrasystolic potentiation effect; and means responsive to said detecting means for adjusting said selectively providing means to vary a parameter of said triggered pacing pulses accordingly.

20. The pacemaker of claim 19 wherein said adjusting means comprises means for selectively varying the ratio of said triggered pacing pulses to a total number of pacing pulses and sensed depolarizations.

21. The pacemaker of claim 19 wherein said adjusting means comprises means for selectively varying said triggered pulse interval to reduce or increase post-extrasystolic effects.

22. The pacemaker of claim 19 wherein said detecting means comprises means for detecting the level of cardiac stress resulting from said post-extrasystolic potentiation effect.

23. The pacemaker of claim 19 wherein said detecting means comprises means for detecting the level of cardiac performance resulting from said post-extrasystolic potentiation effect.

24. A cardiac pacemaker having escape interval timer means for generating a pace event signal at the time-out of an escape interval, sensing means for providing a sense event signal upon sensing a heart depolarization, means for resetting said escape interval timer means in response to said pace and sense event signals, pulse generator means responsive to a pace event signal for generating a pacing pulse, and means for applying the pacing pulse to a heart, further comprising means for selectively providing post-extrasystolic potentiation effects without undue cardiac stress comprising:

means for causing said pulse generator means to provide a post-extrasystolic potentiation inducing packing pulse a coupled pulse interval after the occurrence of a sense event signal in order to induce a post-extrasystolic potentiation effect;

means for detecting a physiologic response resulting from said post-extrasystolic potentiation effect; and means responsive to said detecting means for adjusting said selectively providing means to vary a parameter of said post-extrasystolic potentiation inducing pacing pulses pacing pulses accordingly.

25. The pacemaker of claim 24 wherein said adjusting means comprises means for selectively varying the ratio of said post-extrasystolic potentiation inducing pacing pulses to total pacing pulses and sensed depolarizations.

26. The pacemaker of claim 24 wherein said adjusting means comprises means for selectively varying said coupled pulse interval to reduce or increase post-extrasystolic effects.

27. The pacemaker of claim 24 wherein said detecting means comprises means for detecting the level of cardiac stress resulting from sag post-extrasystolic potentiation effect.

28. The pacemaker of claim 24 wherein said detecting means comprises means for detecting the level of cardiac performance resulting from said post-extrasystolic potentiation effect.

* * * * *